(12) United States Patent
Ojima et al.

(10) Patent No.: US 10,550,418 B2
(45) Date of Patent: Feb. 4, 2020

(54) CELL IDENTIFICATION DEVICE AND PROGRAM

(71) Applicant: SHIMADZU CORPORATION, Kyoto-shi, Kyoto (JP)

(72) Inventors: Noriyuki Ojima, Tokyo (JP); Koretsugu Ogata, Nagaokakyo (JP); Keisuke Shima, Otsu (JP); Hiroto Tamura, Kani (JP); Akifumi Hosoda, Nagoya (JP); Yudai Hotta, Kakegawa (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 16/456,971

(22) Filed: Jun. 28, 2019

(65) Prior Publication Data

US 2019/0323054 A1    Oct. 24, 2019

Related U.S. Application Data

(62) Division of application No. 14/352,496, filed as application No. PCT/JP2012/076841 on Oct. 17, 2012, now Pat. No. 10,385,379.

(30) Foreign Application Priority Data

Oct. 18, 2011 (JP) ................... 2011-229226

(51) Int. Cl.
*C12Q 1/04* (2006.01)
*G16C 20/20* (2019.01)
(Continued)

(52) U.S. Cl.
CPC ............. *C12Q 1/04* (2013.01); *G01N 15/10* (2013.01); *G01N 33/48735* (2013.01);
(Continued)

(58) Field of Classification Search
None
See application file for complete search history.

(56) References Cited

U.S. PATENT DOCUMENTS

| 4,008,388 A | 2/1977 | McLafferty et al. |
| 7,020,559 B1 | 3/2006 | Demirev et al. |

(Continued)

FOREIGN PATENT DOCUMENTS

| CN | 1234906 A | 11/1999 |
| JP | 2006-191922 A | 7/2006 |

(Continued)

OTHER PUBLICATIONS

International Search Report of PCT/JP2012/076841, dated Jan. 29, 2013.

(Continued)

*Primary Examiner* — Sujoy K Kundu
*Assistant Examiner* — Brent A. Fairbanks
(74) *Attorney, Agent, or Firm* — Sughrue Mion, PLLC

(57) ABSTRACT

An apparatus that identifies the type of a test cell based on a result obtained by performing mass spectrometry on the test cell includes a higher-level database, which contains mass lists that each list ion mass values of constituent components of a known cell, and a lower-level database, which contains partial mass lists that each list only strain-specific ion mass values out of the ion mass values. The higher-level database is first searched for a test mass list which is created from the result of the mass spectrometry performed on the test cell, and based on a result of the search, an organism species to be searched in the following search operation is determined. Mass values common to the organism species are subsequently deleted from the mass list for the test cell, and the mass list having undergone the deletion operation is used to search the lower-level database.

3 Claims, 7 Drawing Sheets

(51) Int. Cl.
*G01N 33/487* (2006.01)
*H01J 49/02* (2006.01)
*G01N 15/10* (2006.01)

(52) U.S. Cl.
CPC ............ *G16C 20/20* (2019.02); *H01J 49/025* (2013.01); *G01N 2015/1006* (2013.01)

(56) References Cited

U.S. PATENT DOCUMENTS

| | | | |
|---|---|---|---|
| 7,359,805 | B1 | 4/2008 | Cetto |
| 2002/0120404 | A1 | 8/2002 | Parker |
| 2005/0063864 | A1 | 3/2005 | Sano et al. |
| 2005/0112590 | A1 | 5/2005 | Boom et al. |
| 2009/0006002 | A1 | 1/2009 | Honisch et al. |
| 2012/0197535 | A1 | 8/2012 | Goodiett et al. |
| 2013/0054603 | A1 | 2/2013 | Birdweii |

FOREIGN PATENT DOCUMENTS

| | | |
|---|---|---|
| JP | 2007-316063 A | 12/2007 |
| WO | 2006/048677 | 5/2006 |

OTHER PUBLICATIONS

Extended European Search Report dated Feb. 23, 2015 in European Patent Application No. 12842520.4.
Degand N. et al. (2008) "Matrix-assisted laser desorption ionization—time of flight mass spectrometry for identification of nonfermenting gram-negative bacilli isolated from cystic fibrosis patients", Journal of Clinical Microbiology, vol. 46, No. 10, pp. 3361-3367.
Marklein G. et al. (2009) "Matrix-Assisted Laser Desorption Ionization—Time of Flight Mass Spectrometry for Fast and Reliable Identification of Clinical Yeast Isolates", Journal of Clinical Microbiology, vol. 47, No. 9, pp. 2912-2917.
Sandrin T. R. et al. (2012) "MALDI TOF MS profiling of bacteria at the strain level: A review", Mass Spectrometry Reviews, vol. 32, No. 3, pp. 188-217.
Communication dated Nov. 1, 2016 from the State Intellectual Property Office of the P.R.C. in counterpart application No. 201280051541.6.
Communication dated Feb. 16, 2016 from the State Intellectual Property Office of the People's Republic of China in counterpart application No. 201280051541.6.
Chinese Office Action dated Aug. 12, 2015 in Chinese Patent Application No. 201280051541.6.
Communication dated Jul. 25, 2017 issued by the State Intellectual Property Office of the People's Republic of China in counterpart application No. 201280051541.6.
Chinese Office Action dated Dec. 5, 2014 in Chinese Patent Application No. 201280051541.6.

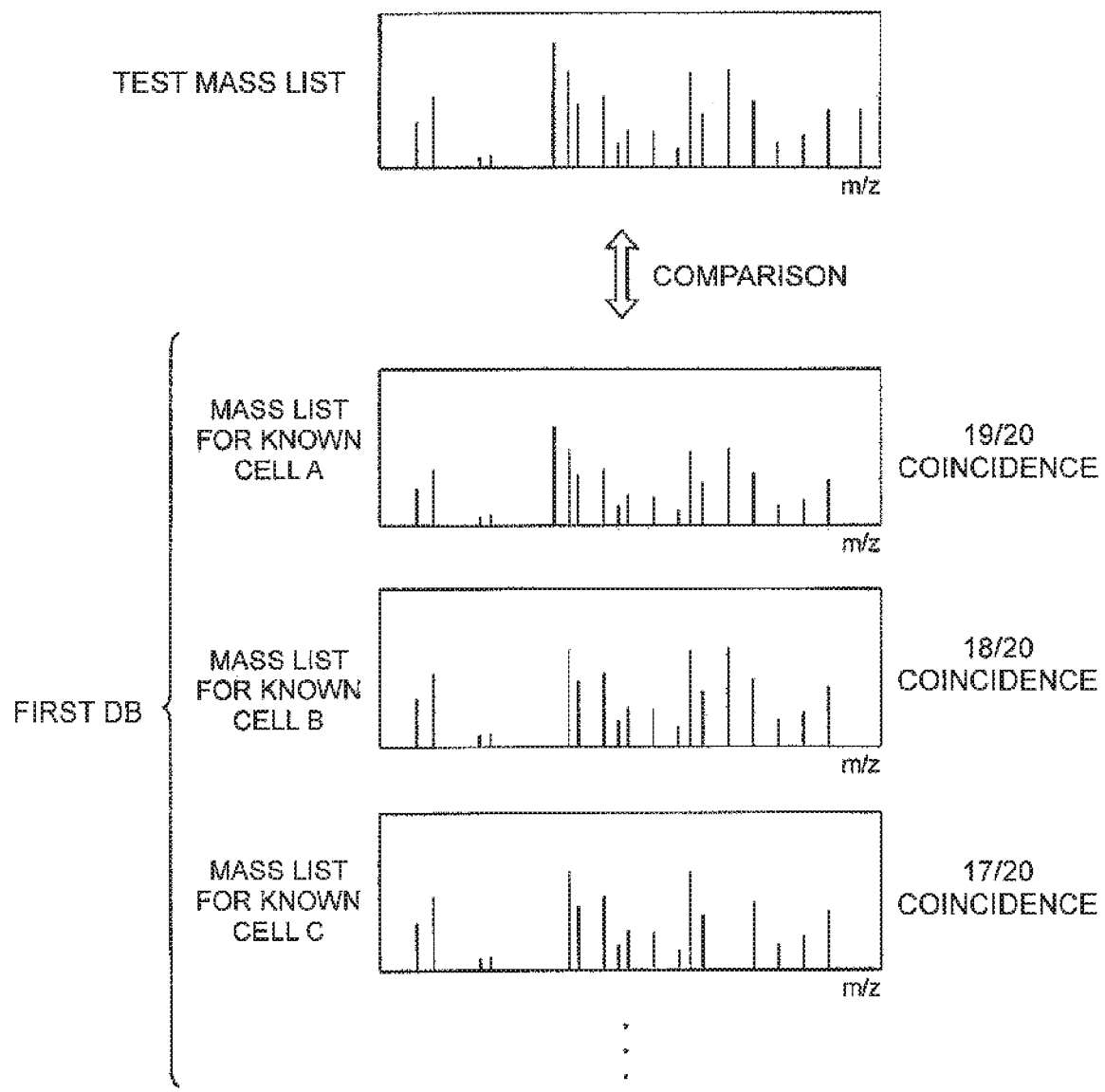

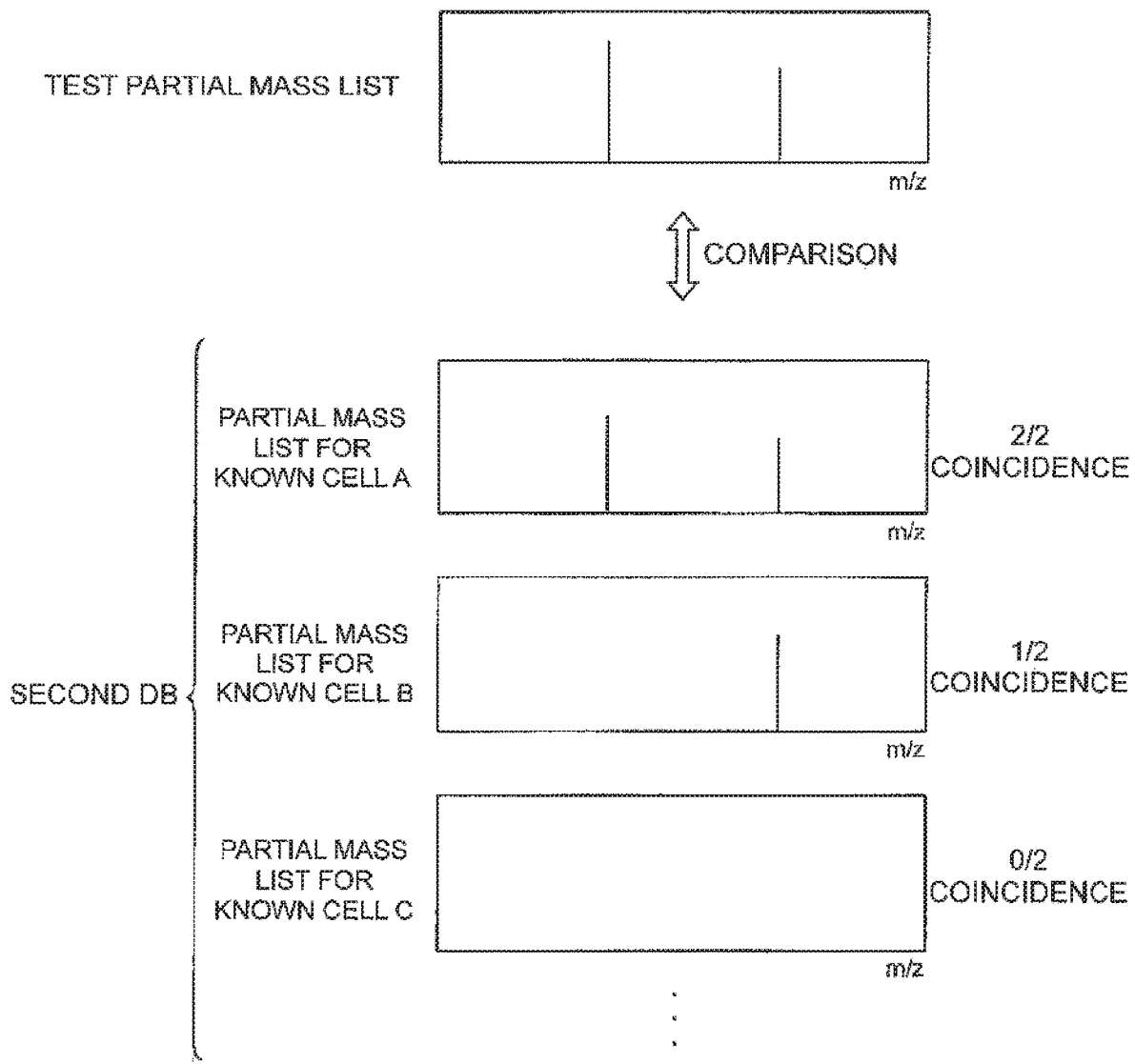

CELL IDENTIFICATION DEVICE AND PROGRAM

CROSS REFERENCE TO RELATED APPLICATIONS

This application is a divisional application based on U.S. application Ser. No. 14/352,496, filed Apr. 17, 2014, which is a National Stage of International Application No. PCT/JP2012/076841 filed Oct. 17, 2012, claiming priority based on Japanese Patent Application No. 2011-229226, filed Oct. 18, 2011, the contents of all of which are incorporated herein by reference in their entirety.

TECHNICAL FIELD

The present invention relates to an apparatus and a program for identifying the type of a cell based on a result of mass spectrometry performed on a component derived from the cell.

BACKGROUND ART

There is a known homologous analysis method based on a DNA base sequence as a method for identifying the type of a cell, and the method is widely used, for example, for classification and identification of a microorganism (see Patent Literature 1, for example). The method includes the steps of extracting a DNA from a test cell and determining a DNA base sequence in an area that is highly preserved in every organism, such as a rRNA gene. The method further includes the steps of searching a database containing a large number of data on DNA base sequences of known cells for the determined DNA base sequence, and picking up a base sequence showing high similarity to the DNA base sequence in the test cell. The method finally includes the step of determining that an organism species from which the selected base sequence is derived is the same species as the test cell or a species related to the test cell.

The method of this type using a DNA base sequence, however, requires relatively long time to extract a DNA from a test cell and to determine a DNA base sequence, and therefore has a difficulty in performing a quick cell identification.

In view of the fact described above, a method of identifying a cell based on a mass spectrum pattern obtained by performing mass spectrometry on a test cell has been increasingly used in recent years (see Patent Literature 2, for example). The method includes a step of first analyzing a solution containing proteins extracted from a test cell or a suspension liquid containing the test cell with a mass spectrometer using MALDI-MS (matrix assisted laser desorption/ionization-mass spectrometry) or any other mild ionizing method. The method further includes a step of comparing the resultant mass spectrum pattern with mass spectrum patterns of known cells contained in a database to identify the test cell. Mass spectrometry not only quickly provides an analysis result from a trace amount of cell specimen but also readily allows successive analysis of a large number of specimens. The cell identification method of this type using mass spectrometry therefore allows cell identification to be readily and quickly performed.

CITATION LIST

Patent Literature

[Patent Literature 1] JP-A-2006-191922
[Patent Literature 2] JP-A-2007-316063

SUMMARY OF INVENTION

Technical Problem

In the cell identification method using mass spectrometry described above, cell identification is typically performed by primarily looking at information on the mass values of a group of ribosomal proteins. However, since the group of ribosomal proteins generally has a high preserving ability of amino acid sequences, when cells that belong to the same organism species undergo mass spectrometry, most peaks appear at the same mass values in a mass spectrum. The cell identification method using mass spectrometry, which can identify a difference at a cell species level, therefore has a difficulty in some cases in identifying a difference at a strain level, which is a classification level below the species classification level.

The present invention has been made to solve the problem described above. An object of the present invention is to provide a cell identification apparatus capable of precise, quick cell identification at the strain level.

Solution to Problem

A cell identification apparatus according to a first aspect of the present invention that has been made to solve the problem described above is an apparatus that includes a storage section and a computation section and identifies the type of a test cell based on a result obtained by performing mass spectrometry on the test cell, the apparatus characterized in that the storage section stores a first database containing mass lists for a plurality of known cells, each of the mass lists listing ion mass values or molecular weights of constituent components of each of the plurality of known cells, and a second database containing partial mass lists for the plurality of known cells, each of the partial mass lists listing, among the ion mass values or molecular weights of the constituent components of the known cells, ion mass values or molecular weights other than ion mass values or molecular weights common to classification groups in a predetermined class to which the known cells belong, and the computation section includes a) first search means for searching the first database for a test mass list which is created from a result of the mass spectrometry and which lists ion mass values or molecular weights of constituent components of the test cell, b) classification group determination means for determining, based on a result of the search performed by the first search means, one of the classification groups in the class as a classification group to be searched in the following search operation, c) test partial mass list creation means for creating a test partial mass list from the test mass list by deleting ion mass values or molecular weights common to the classification group determined by the classification group determination means, and d) second search means for searching the second database for the test partial mass list created by the test partial mass list creation means.

The classification group determination means described above may automatically select a mass list having high similarity to the test mass list as a result of the search performed by the first search means and determine the mass list as a classification group to be searched in the following search operation, or may make a display section, such as a monitor, to display the result of the search performed by the first search means, allow a user to specify a classification group, and determine, as a classification group to be searched in the following search operation, a classification group specified by the user who operates a keyboard or any other input device based on the search result.

The principle of cell identification by using the cell identification apparatus according to the present invention will be described with reference to FIG. 6 and FIG. 7. The cell identification apparatus according to the present invention includes a first database (first DB) and a second database (second DB), in each of which mass lists on a plurality of known cells, such as those shown in FIG. 6, and partial mass lists on the plurality of known cells, such as those shown in FIG. 7, are registered. The mass list used herein is a list that lists the ion mass values or molecular weights of each constituent component of a cell and can be created, for example, by performing mass spectrometry on a cell and listing mass values (m/z in exact sense) corresponding to peaks in the resultant mass spectrum. On the other hand, the partial mass list used herein is a list that lists, among the ion mass values or molecular weights of the constituent components of a cell, ion mass values or molecular weights other than those common to a classification group in a predetermined classification class (species classification hierarchy) to which the cell belongs. A partial mass list can be created, for example, by deleting, from the mass list created for a cell, ion mass values or molecular weights commonly contained in a species to which the cell belongs. In FIG. 6 and FIG. 7, each of the mass lists and the partial mass lists contains information on the mass value and height at each peak that appears in a mass spectrum, but a mass list in the present invention does not necessarily contain the information on the height of each peak (that is, quantity proportion of each existing constituent component).

In the cell identification apparatus according to the present invention, the first database is first searched by using a mass list (test mass list) created from a result obtained by performing mass spectrometry on a test cell. The test mass list and each mass list in the first database list a large number of mass values, as shown in FIG. 6, but most of the mass values are the same in genetically related cells (cells of organisms that belong to the same species, for example). For example, in the case shown in FIG. 6, a mass list for a known cell A contains 19 out of 20 mass values listed in the test mass list, a mass list for a known cell B contains 18 out of the 20 mass values, and a mass list for a known cell C contains 17 out of the 20 mass values. The proportion of the mass values contained in the mass list for each of the known cells to the mass values listed in the test mass list is 19/20=0.95 for the known cell A, 18/20=0.9 for the known cell B, and 17/20=0.85 for the known cell C, which are close to each other (it is noted in FIG. 6 that the number of mass values contained in each of the mass lists is reduced for ease of illustration, but an actual mass list lists a greater number of mass values, which means that the difference in the proportion described above between genetically related cells is further reduced).

As described above, the search of the first database results in a small difference in a comparison result between the test cells and genetically related known cells. Since a conventional cell identification apparatus, however, only performs search corresponding to the search of the first database for cell identification at a species level, it is typically difficult to perform precise cell identification at a strain level.

In contrast, in the cell identification apparatus according to the present invention, a classification group (species, for example) to which a test cell belongs is determined based on a result of the search of the first database, and mass values commonly present in the classification group are deleted from the test mass list. A partial mass list for the test cell (test partial mass list), such as that shown in the upper portion of FIG. 7, is thus created. The test partial mass list is then used to search the second database. As described above, in partial mass lists contained in the second database, among the ion mass values (or molecular weights) of the constituent components of each of the known cells, those common to a classification group in a predetermined class to which the known cells belong are deleted. Each of the partial mass lists in the second database therefore only lists mass values specific to the classification group to which the test cell belongs (classification group one class below the classification group determined by the classification group determination means, strain, for example), and the total number of listed mass values is greatly smaller than that in the mass list described above. As a result, in the search of the second database, the difference in comparison result between the test cell and genetically related cells increases. For example, in the case shown in FIG. 7, the proportion of the mass values contained in the partial mass list for each of the known cells to the mass values listed in the test partial mass list is 2/2=1 for the known cell A, 1/2=0.5 for the known cell B, and 0/2=0 for the known cell C, showing larger differences between the known cells than the case shown in FIG. 6. The search of the second database therefore allows precise extraction of a cell more related to the test cell from a plurality of genetically related known cells, resulting in precise cell identification at a strain level, which is difficult by a conventional apparatus.

The cell identification apparatus according to the present invention can be configured to perform not only two-stage search of the first database and the second database as described above but also two-stage search of a single database.

That is, a cell identification apparatus according to a second aspect of the present invention that has been made to solve the problem described above is an apparatus that includes a storage section and a computation section and identifies the type of a test cell based on a result obtained by performing mass spectrometry on the test cell, the apparatus characterized in that the storage section stores a database containing mass lists for a plurality of known cells, each of the mass lists listing ion mass values or molecular weights of constituent components of the known cell, the computation section includes a) first search means for searching the database for a test mass list which is created based from a result of the mass spectrometry and which lists ion mass values or molecular weights of constituent components of the test cell, b) classification group determination means for determining, based on a result of the search performed by the first search means, a classification group to be searched in the following search operation, c) test partial mass list creation means for creating a test partial mass list from the test mass list by deleting ion mass values or molecular weights common to the classification group determined by the classification group determination means, and d) second search means for searching, among the mass lists contained in the database, mass lists for known cells which belong to the classification group determined by the classification group determination means for the test partial mass list, wherein the second search means deletes, from the mass lists to be searched, ion mass values or molecular weights common to the classification group determined by the classification group determination means and searches the mass lists having undergone the deletion operation for the test partial mass list.

Advantageous Effects of Invention

As described above, the cell identification apparatus according to the present invention allows precise extraction of a cell more related to a test cell from a plurality of genetically related known cells. The cell identification apparatus according to the present invention can therefore readily and quickly perform precise cell identification at a strain level, which is difficult by a conventional apparatus.

BRIEF DESCRIPTION OF THE DRAWINGS

FIG. 6 is a conceptual diagram for describing search of a first database.

FIG. 7 is a conceptual diagram for describing search of a second database.

DESCRIPTION OF EMBODIMENTS

Some modes for implementing a cell identification apparatus according to the present invention will be described below with reference to examples.

EXAMPLES

Example 1

Figure 1:
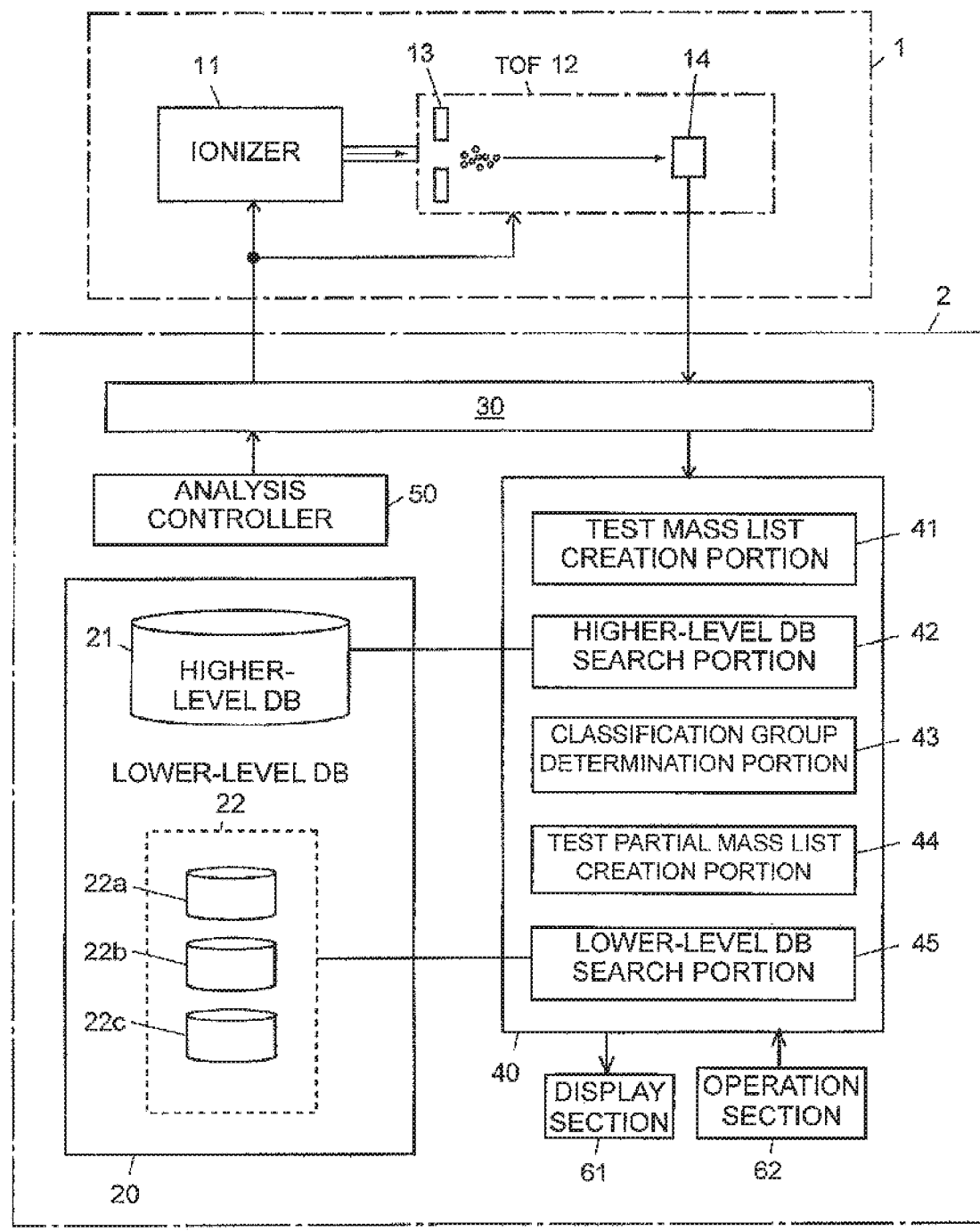
FIG. 1 is a configuration diagram showing key portions of a cell identification system according to a first example of the present invention.
Figure 2:
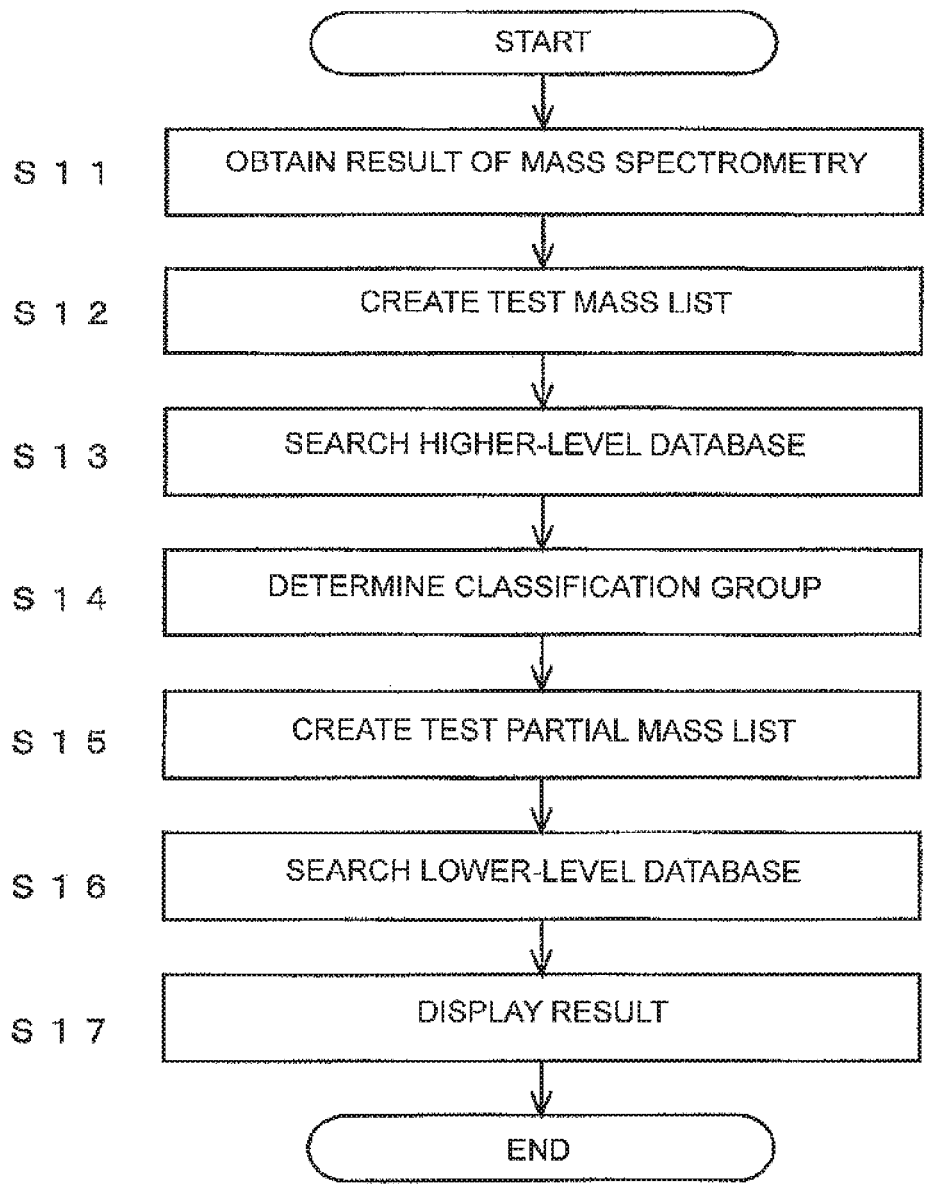
FIG. 2 is a flowchart showing the action of the cell identification system according to the first example.

FIG. 1 is an overall view of a cell identification system including a cell identification apparatus according to the present example, and FIG. 2 is a flowchart showing the procedure of cell identification using the present system.

The cell identification apparatus according to the present example generally includes a mass spectrometry unit 1 and a cell identification unit 2. The mass spectrometry unit 1 includes an ionizer 11, which ionizes molecules and atoms in a specimen based on matrix assisted laser desorption/ionization (MALDI), and a time-of-flight mass separator (TOF) 12, which separates a variety of ions ejected from the ionizer 11 according to their mass values.

The TOF 12 includes extracting electrodes 13, which extracts ions from the ionizer 11 and guides the ions into an ion flight space in the TOF 12, and a detector 14, which detects ions having undergone the mass separation in the ion flight space.

The cell identification unit 2 includes a storage section 20, which stores a database to be searched, an interface 30, through which information is sent and received to and from the mass spectrometry unit 1 via a communication line, a computation section 40, which searches the database based on a detection signal outputted from the detector 14 in the mass spectrometry unit 1, and an analysis controller 50, which controls the action of the mass spectrometry unit 1.

The storage section 20 is formed of a large capacity storage device, such as a hard disk drive, and stores two types of database, a higher-level database 21 and a lower-level database 22. The higher-level database 21 and the lower-level database 22 correspond to a first database and a second database in the present invention, respectively.

A large number of mass lists on known microorganisms are registered in the higher-level database 21. Each of the mass lists in the present example lists the mass values of ions detected when mass spectrometry is performed on a microorganism cell and contains not only information on the mass values of the ions but also at least information (classification information) on a classification group (genus, species, and strain) to which the microorganism cell belongs. Each of the mass lists is desirably created based on data obtained by actually performing mass spectrometry on a variety of microorganism cells in advance (measured data) under the same conditions of the ionizing method and the mass separation method used by the mass spectrometry unit 1.

To create a mass list from the measured data, peaks that appear within a predetermined mass range are first extracted from a mass spectrum obtained as the measured data. In this process, setting a mass range from about 4,000 to 15,000 allows extraction of peaks derived primarily from proteins. Further, extracting only peaks each having a height (relative intensity) greater than or equal to a predetermined threshold allows removal of undesired peaks (noises). Since a large number of ribosomal protein groups are expressed in a cell, appropriately setting the threshold allows most of the mass values to be listed in a mass list to be derived from the ribosomal proteins. Mass values (m/z) corresponding to the peaks extracted as described above are then listed on a cell basis, followed by addition of the information on the classification and other types of information, and the resultant mass list is registered in the higher-level database 21. To suppress gene expression variations due to incubation conditions, each microorganism cell to be used to collect measured data is desirably handled in an incubation environment which was normalized in advance.

It is difficult to obtain measured data, such as those described above, for all an enormous number of known microorganisms. To address the problem, mass lists for at least part of the microorganisms may be mass lists based on molecular weights determined through calculation (calculated molecular weights), instead of mass lists based on measured data, such as those described above, for registration in the higher-level database 21. In this case, each mass list desirably contains attached information showing which of measured data or calculated molecular weights has been used to create the mass list.

A mass list based on the calculated molecular weights described above is created, for example, as follows:

(1) A DNA base sequence of a gene of a known microorganism (gene of ribosomal protein groups, for example) is obtained from an existing database (DDBJ, EMBL, Gen-Bank, and other public databases, for example), and a calculated molecular weight of each of a variety of proteins contained in a cell of the microorganism is derived by translating the DNA base sequence into an amino acid sequence. Further in this process, the calculated molecular weight may be corrected in consideration of cutting of N-terminal initiation methionine residue, post-translational modification, or correction of the amino acid sequence made based on bioinformatic engineering homologous analysis, and the corrected value may be used to create a mass list in addition to or in place of the pre-correction calculated molecular weight. The "correction of the amino acid sequence made based on bioinformatic engineering homologous analysis" described above means as follows: An existing database or any other data is first searched for gene sequence s highly homologous to a gene sequence of a target microorganism by using BLAST or any other type of homologous analysis. A correct translation area is then estimated by referring to an annotated gene sequence among the resultant gene sequence s. The amino acid sequence is then corrected based on the estimated translation area, and a calculated molecular weight is calculated from the corrected amino acid sequence.

In a case where the existing database described above contains a calculated molecular weight of a protein contained in each of a variety of microorganism cells, the calculated molecular weight may be obtained from the database and used to create a mass list. In this case as well, the calculated molecular weight is corrected in consideration of cutting of N-terminal initiation methionine residue, post-translational modification, or correction of the amino acid sequence made based on bioinformatic engineering homologous analysis.

Even when a mass list is created based on measured data as described above, the mass list is desirably registered in the higher-level database after a calculated molecular weight is calculated by using the same method described above and each mass value in the mass list is compared with the calculated molecular weight for validity of the mass value. The reliability of data in the higher-level database 21 can thus be increased. When a result of the comparison with the calculated molecular weight shows that the mass list is not valid, it is desirable that each mass value in the mass list is corrected based on the calculated molecular weight or the mass spectrometry is performed again to create a new mass list.

(2) The calculated molecular weight determined in step (1) described above is converted into ion mass, and the ion mass is used to create a mass list. When a living body specimen is analyzed by using MALDI-TOFMS, it is known that molecular weight-related ions, such as $[M+H]^+$ (M stands for molecule and H stands for hydrogen atom), $[M-H]^-$, or $[M+Na]^+$ (Na stand for sodium atom), are primarily detected. The calculated molecular weight can therefore be readily converted into ion mass as long as mass spectrometry conditions are known. For example, when a living body specimen prepared by using sinapic acid as a matrix agent is analyzed by using MALDI-TOFMS, a peak of a protonated molecule ($[M+H]^+$) is primarily observed. In this case, the calculated molecular weight determined in step (1) described above can therefore be converted into ion mass by adding the mass of a proton to the calculated molecular weight.

The lower-level database 22 contains a plurality of sub-databases 22a, 22b, 22c, . . . divided on a microorganism species basis. Each of the sub-databases 22a, 22b, 22c, . . . contains partial mass lists on one or more microorganism cells that belong to a single species. The partial mass list in the present example is a list which lists ion mass values obtained by deleting mass values commonly detected in a species to which the microorganism belongs from the mass values detected when mass spectrometry is performed on a microorganism cell. Such a partial mass list can be created by extracting mass lists for microorganisms that belong to the same species from a large number of mass lists on known microorganisms created by using the method described above and deleting mass values commonly contained in the extracted mass lists from each of the mass lists. Therefore, if only one mass list of a microorganism that belongs to a single species is registered in the higher-level database, the mass list registered in the higher-level database 21 and a partial mass list registered in the lower-level database 22 have the same mass values.

The computation section 40 searches the higher-level database 21 and the lower-level database 22 based on a result obtained by analyzing a specimen containing constituent components of a test cell in the mass spectrometry unit 1. The computation section 40 includes the following functional blocks: a test mass list creation portion 41, higher-level DB search portion 42, a classification group determination portion 43, a test partial mass list creation portion 44, and a lower-level DB search portion 45 (the function of each of the portions will be described later). The higher-level DB search portion 42 corresponds to first search means in the present invention, and the lower-level DB search portion 45 corresponds to second search means in the present invention. The cell identification unit 2 in the present example is actually a computer including a CPU, a memory, and other components, and the CPU executes a predetermined control/processing program installed in the computer to achieve the functions of each of the functional blocks by software. The computation section 40 is connected not only to the mass spectrometry unit 1 via the interface 30 but also to an operation section 62, which includes a keyboard, a mouse, or any other pointing device, and a display section 61, such as a liquid crystal display.

The procedure in accordance with which the species and strain of a microorganism is identified by using the cell identification system of the present example will next be described with reference to FIG. 2.

A user first prepares a specimen containing constituent components of a test cell and places the specimen in the mass spectrometry unit 1 for mass spectrometry. In this process, the specimen can be a cell extract, cell constituent components, such as ribosomal proteins, purified from a cell extract, or a fungus body or a cell suspension as a whole. It is, however, noted that the specimen is desirably prepared under the same conditions as those under which the mass lists in the higher-level database 21 are created based on the measured data.

The test mass list creation portion 41 obtains detection signals which are obtained from the detector 14 in the mass spectrometry unit 1 via the interface 30 (step S11). The test mass list creation portion 41 creates a mass spectrum based on the detection signals and extracts peaks that appear in the mass spectrum to create a mass list containing information on the mass (m/z in exact sense) corresponding to each of the peaks (the mass list is hereinafter referred to as a "test mass list") (step S12). Peak extraction conditions in this process (such as a mass range to be extracted and a threshold of peak intensity) are also desirably the same as those under which the mass lists in the higher-level database 21 are created based on the measured data.

The higher-level DB search portion 42 subsequently searches the higher-level database 21 for the test mass list to extract mass lists for known microorganisms that each has a mass pattern similar to that of the test mass list, for example, mass lists containing a large number of mass values that coincide with mass values in the test mass list within a predetermined error range (step S13).

The classification group determination portion 43 subsequently refers to the information on the classification group described in each of the mass lists extracted in step S13 to identify an organism species to which a known microorganism corresponding to the mass list belongs. The organism species is then assumed to be an organism species to which the test cell belongs, and the organism species is determined as a classification group to be searched for in the following search operation (step S14).

After the organism species to which the test cell belongs is determined as described above, the test partial mass list creation portion 44 deletes mass values commonly detected in the organism species (mass values common to species) from the test mass list (step S15). The resultant mass list is called a "test partial mass list." The mass values common to species are desirably determined on an organism species basis in advance and stored in the storage section 20. Instead, when an organism species to which the test cell belongs is determined, the test partial mass list creation portion 44 may obtain mass lists for the known microorganisms that belong to the organism species from the higher-level database, compare the test mass list with the obtained mass lists to determine mass values common to the species, and use the mass values common to the species to create the test partial mass list.

The lower-level DB search portion 45 subsequently selects a sub-database (sub-database 22a, for example) corresponding to the organism species determined by the classification group determination portion 43 as a search target. The sub-database 22a is searched for the test partial mass list (step S16), and a partial mass list having a high similarity to the test partial mass list is extracted from the sub-database. In this process, only one partial mass list having the highest similarity may be extracted, or partial mass lists having similarities higher than a predetermined threshold or a predetermined number of partial mass lists in descending order of the similarity may be extracted.

The lower-level DB search portion 45 subsequently outputs information on the partial mass list extracted in the search operation described above as a search result in the display section 61 (step S17). The information displayed in this process includes at least the name of the strain of the known microorganism described in the partial mass list and the similarity to the test partial mass list. The user can thus recognize the name of the strain of the known microorganism that provides a mass pattern similar to that of the test cell, and estimate that the test cell belongs to the same strain of the known microorganism or a strain genetically related to the known microorganism.

The information contained in the partial mass list and displayed in step S17 desirably includes information representing which of measured data or a calculated molecular weight the partial mass list has been created based on. In general, a mass list created based on measured data is more correct. Therefore, when a plurality of partial mass lists is displayed as a search result, the user can refer to the information to determine which partial mass list is more appropriate as a search result.

Example 2

Figure 3:
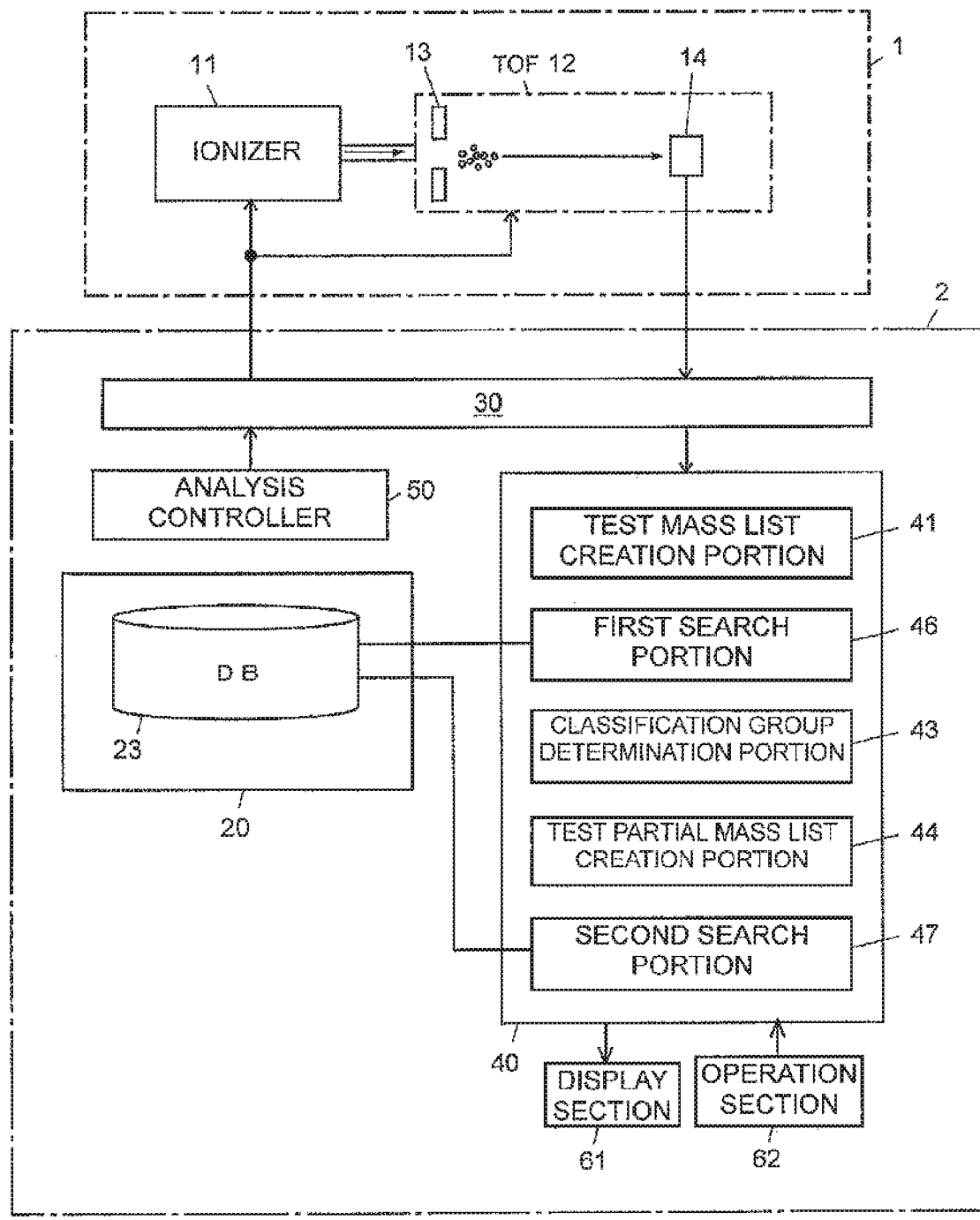
FIG. 3 is a configuration diagram showing key portions of a cell identification system according to a second example of the present invention.
Figure 4:
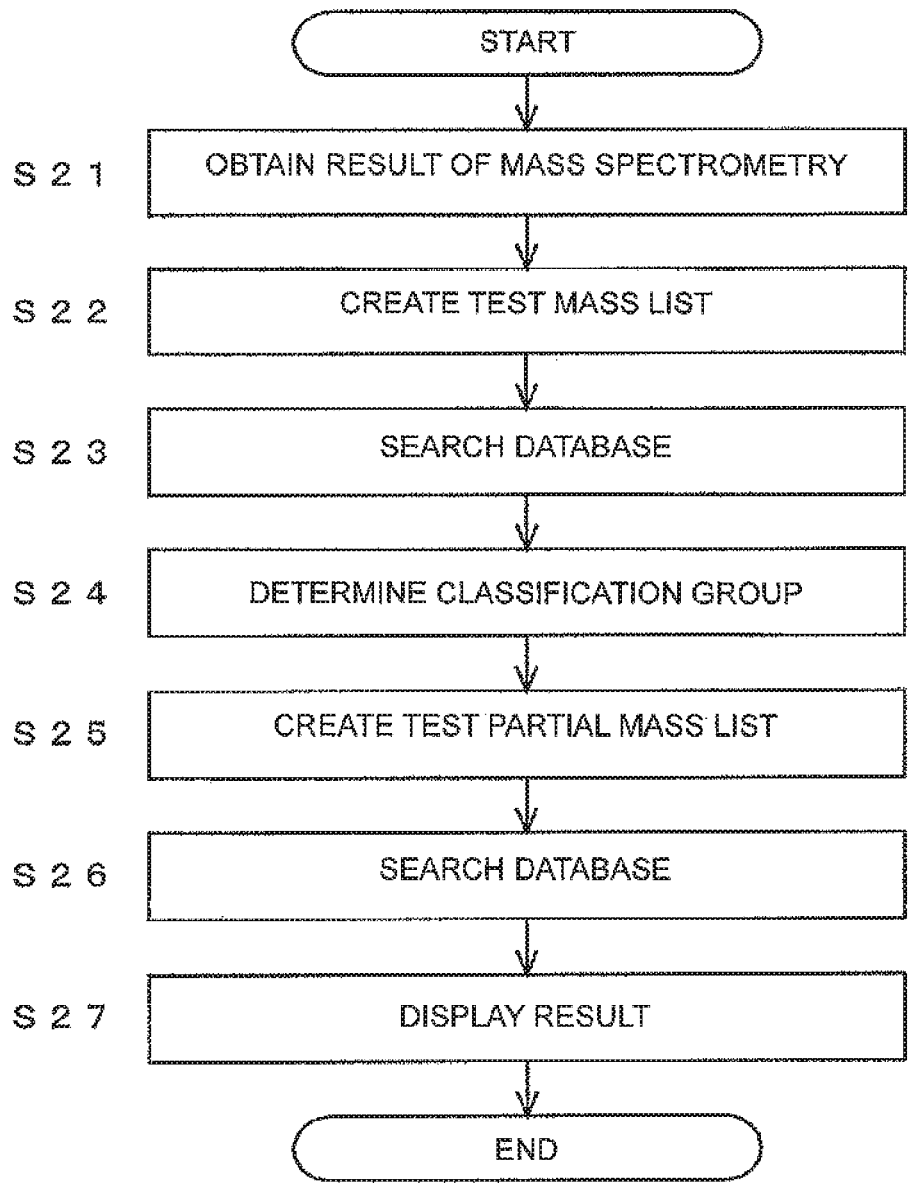
FIG. 4 is a flowchart showing the action of the cell identification system according to the second example.

The first example described above shows the cell identification apparatus including the two databases, the higher-level database 21 and the lower-level database 22, but a cell identification apparatus according to the present example may include only one database. An example of a thus configured cell identification apparatus will be described below with reference to FIG. 3 and FIG. 4. FIG. 3 is an overall view of a cell identification system including the cell identification apparatus according to the present example, and FIG. 4 is a flowchart showing the procedure of cell identification using the present system.

The cell identification system according to the present example has the same configuration as that in the first example except that the higher-level database 21 and the lower-level database 22 are replaced with a single database 23 and the higher-level DB search portion 42 and the lower-level DB search portion 45 are replaced with a first search portion 46 and a second search portion 47.

The database 23 in the present example corresponds to the higher-level database 21 in the first example and contains a large number of mass lists on known microorganisms, as the higher-level database 21 does.

The first search portion 46 plays the same role as that of the higher-level DB search portion 42 in the first example and searches the database 23 for the test partial mass list created by the test mass list creation portion 41. The second search portion 47 searches the database 23 for the test partial mass list created by the test partial mass list creation portion 44. In this process, the second search portion 47 searches for only the test partial mass list on microorganisms that belong to the classification group determined by the classification group determination portion 43. Further, among the mass values listed in each of the mass lists in the database 23, the second search portion 47 uses mass values other than those commonly contained in the classification group to compare the test partial mass list with mass lists in the database 23.

The procedure for identifying the species and strain of a microorganism by using the cell identification system of the present example will be described with reference to FIG. 4.

A user first places a specimen containing constituent components of a test cell in the mass spectrometry unit 1 and performs mass spectrometry on it. The test mass list creation portion 41 obtains a result of the mass spectrometry (step S21) and creates a test mass list (step S22). The steps described above are the same as the steps S11 and S12 in FIG. 2 and will therefore not be described in detail.

The first search portion 46 then searches the database 23 for the test mass list to extract mass lists for known microorganisms that each has a mass pattern similar to that of the test mass list (step S23).

The classification group determination portion 43 subsequently refers to the classification information described in each of the mass lists extracted in step S23 and identifies an organism species to which a known microorganism corresponding to the mass list belongs. The organism species is then assumed to be an organism species to which the test cell belongs, and the organism species is determined as a classification group to be searched for in the following search operation (step S24).

After the organism species to which the test cell belongs is determined as described above, the test partial mass list creation portion 44 deletes mass values common to the organism species from the test mass list and create a test partial mass list (step S25). The step is the same as step S15 in FIG. 2 and will therefore not be described in detail.

The second search portion 47 then searches the database 23 for the test partial mass list created in step S25 (step S26). In this process, from a large number of mass lists contained in the database 23, the second search portion 47 selects mass lists, as search targets, on microorganisms that belong to the organism species determined in step S24. Further, among the mass values listed in each of the selected mass lists, only mass values specific to each strain of the organism species are used to compare the test partial mass list with the selected mass lists. Specifically, the second search portion 47 identifies mass values commonly contained in each of the mass lists selected as the search targets (mass values common to species) and compares the mass values in each of the mass lists from which the mass values common to species are deleted with the mass values in the test partial mass list and calculate the similarity. As a result, a mass list having a high similarity to the test partial mass list is extracted from the database 23. The second search portion 47 does not necessarily identify the mass values common to species, but the mass values common to species may be identified in advance on a microorganism basis and stored in the storage section 20.

The second search portion 47 then outputs information on the partial mass list extracted in the search operation described above as a search result in the display section 61 (step S27). The information displayed in this process includes at least the name of the strain of the known microorganism described in the partial mass list and the similarity to the test partial mass list. The user can thus recognize the name of the strain of the known microorganism that provides a mass pattern similar to that of the test cell, and estimate that the test cell belongs to the same strain of the known microorganism or a strain genetically related to the known microorganism.

Example 3

Figure 5:
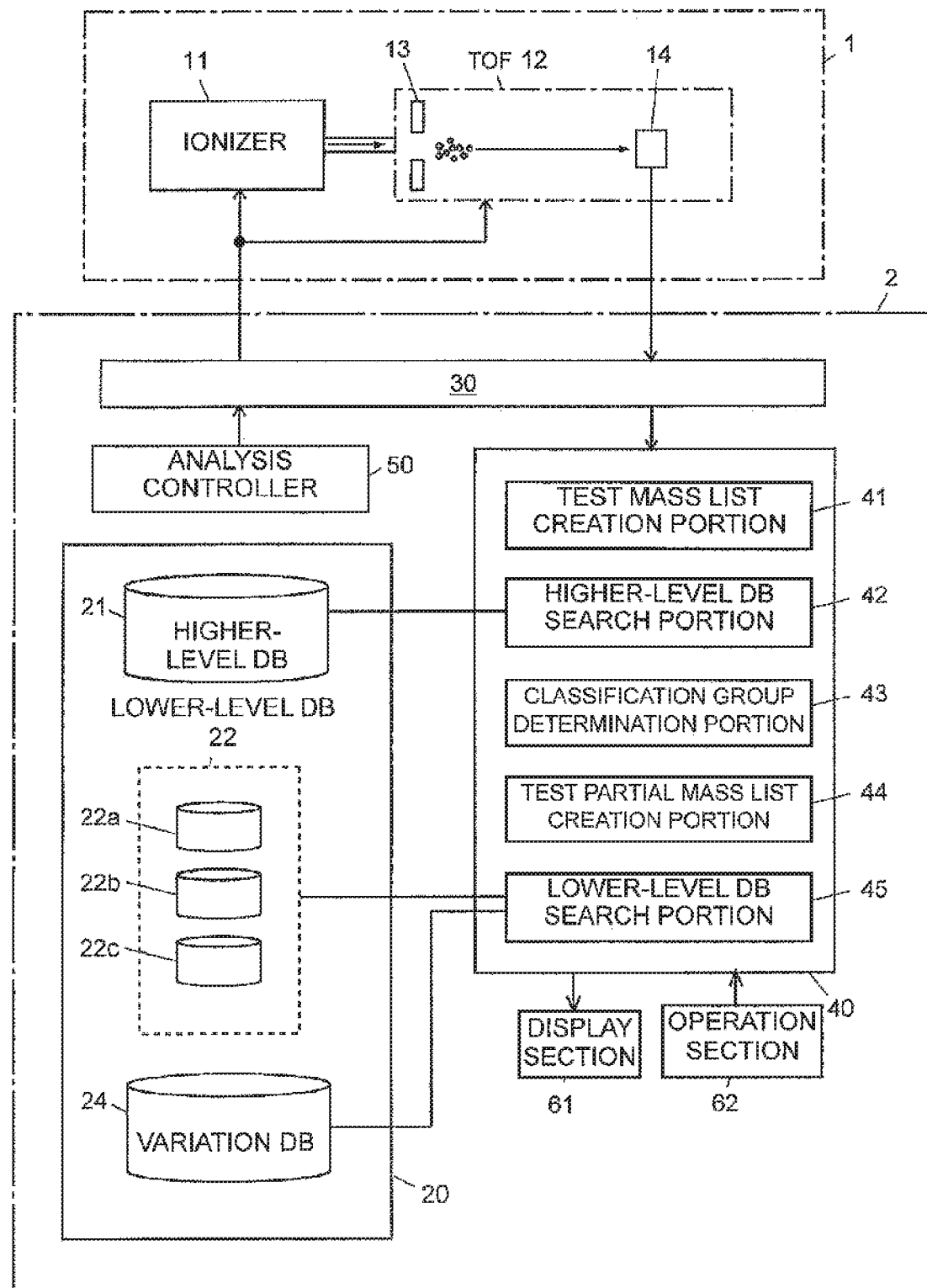
FIG. 5 is a configuration diagram showing key portions of a cell identification system according to a third example of the present invention.

A third example of the cell identification apparatus according to the present invention will be described with reference to FIG. 5. A system of the present example includes a variation database 24, which contains information on variations that can occur in a base sequence or an amino acid sequence (hereinafter referred to as "variation information"), and the lower-level DB search portion 45 performs search operation in consideration of the variations described above.

The variation information described above is registered in advance in the variation database 24. The variation information includes the name of each of variations, the type of amino acid or base and a portion of amino acid or base that undergo the variation, the amount of change in ion mass (m/z) due to the variation, and other types of information.

In the present system, each partial mass list registered in the lower-level database 22 contains information on the amino acid sequence of a protein corresponding to each mass value in the list and/or the base sequence of a gene that codes the protein (hereinafter referred to as "sequence information") as well as the mass information and the classification information described above.

The procedure of cell identification using the cell identification system of the present example is almost the same as that shown in the flowchart of FIG. 2. In step S16, however, the lower-level DB search portion 45 performs not only the same search operation as that in the first example described above (search in consideration of no variation) but also search operation in consideration of variations that may occur in an amino acid sequence or a base sequence.

In the search operation in consideration of variations described above, the lower-level DB search portion 45 first obtains variation information from the variation database 24. In this process, the lower-level DB search portion 45 first obtains from the variation database 24, in which information on a variety of types of variation is registered, information on a single type of variation. The lower-level DB search portion 45 then modifies partial mass lists in a sub-database to be searched (sub-database 22a, for example) based on the variation information and creates partial mass lists to which the variation is applied (the resultant partial mass lists are hereinafter referred to as "modified mass lists"). Specifically, the lower-level DB search portion 45 refers to the sequence information in each partial mass list and determines whether or not the amino acid sequence of a protein corresponding to each mass value listed in the partial mass list (or the base sequence of a gene that codes the protein) has a portion where the variation may occur. When the determination result shows that such a portion is present, the lower-level DB search portion 45 changes the mass value to a mass value after the variation occurs.

The lower-level DB search portion 45 subsequently compares the resultant modified mass list with the test partial mass list and calculates the similarity between mass patterns and temporarily stores the calculated similarity in the storage section 20. The lower-level DB search portion 45 then repeats the creation of a modified mass list and the calculation of the similarity described above for all the type of variation registered in the variation database 24. When the search operation in consideration of all the types of variation is completed, the lower-level DB search portion 45 reads all search results from the storage section 20 and evaluates validity of the results under the guidance, for example, of the similarity. For example, the lower-level DB search portion 45 extracts results each showing a similarity higher than or equal to a fixed value or a predetermined number of results in descending order of the similarity. The display section 61 displays the extracted results on the screen of the display section 61 (step S17).

Performing the search in consideration of variation as described above allows precise search results to be obtained even when a test cell is derived as a variation of a known microorganism strain.

In the example described above, the search is performed in consideration of all the types of variation registered in the variation database 24, but many of the types of variation registered in the variation database 24 actually occur only at very low probabilities. In view of the fact described above, for each type of variation, the degree of priority, importance, and other factors based on the possibility of occurring the variation may be registered in the variation database 24, and the user may select, for example, a predetermined number (which is specified by the user) of types of variation in descending order of the priority, followed by search operation in consideration of the selected types of variation. Instead, before the search of the lower-level database 22, a list of the types of variation registered in the variation database 24 may be displayed on the display section 61, and the user may be prompted to select types of variation from the list for the following search operation. Still instead, the search operation may be terminated at a point during the search of the lower-level database 22 when a partial mass list having a fairly high similarity is obtained. In this case, the lower-level DB search portion 45 is configured to stop repeating the database search at a point when a partial mass list or a modified mass list having a similarity to the test partial mass list greater than or equal to a predetermined threshold is searched, whereby it can be expected that the search time is significantly shortened.

The present example has been described with reference to the case where an apparatus that searches the higher-level database 21 and the lower-level database 22, such as the apparatus according to the first example, performs the search in consideration of variation. Further, in an apparatus that performs two-stage search on the single database 23, such as the apparatus according to the second example, providing the same variation database described above in the storage section 20 also allows the search in consideration of variation to be performed. In this case, among the mass values listed in the mass lists in the database 23, at least strain-specific mass values are listed with sequence information, such as that described above. The second search portion 47 then performs the search operation in consideration of the types of variation registered in the variation database.

Some modes for carrying out the present invention have been described with reference to the examples, but the present invention is not limited to the examples described above and changes can be made to those as appropriate to the extent that the changes fall within the scope of the present invention. For example, in the examples described above, a cell identification system including a mass spectrometry unit formed of a combination of an ionizer based on matrix assisted laser desorption/ionization (MALDI) and a time-of-flight mass separator (TOF) has been shown by way of example. The mass spectrometry unit does not necessarily have the configuration described above and may have any configuration capable of ionizing and detecting a molecule having a mass value ranging between about 1,000 and 25,000. For example, the ionizer can instead be based on electro-spray ionization (ESI), laser desorption electro-spray ionization (LDESI), matrix assisted laser desorption/electro-spray ionization (MALDESI), paper spray ionization (PSI), atmospheric pressure chemical ionization (APCI), or electric impact ionization (EI).

In the examples described above, species-level cell identification is performed in the first search operation using the higher-level DB search portion 42 or the first search portion 46, and strain-level cell identification is performed in the second search operation using the lower-level DB search portion 45 or the second search portion 47, but the cell identification is not necessarily performed as described above. For example, genus-level cell identification may be performed in the first search operation, and the species-level cell identification may be performed in the second search operation.

Further, in the examples described above, mass lists or partial mass lists registered in each database lists the ion mass values of constituent components of a cell, but ion mass values are not necessarily listed. For example, the molecular weights of constituent components of a cell may be listed. In this case, when the test mass list creation portion 41 creates a test mass list, the mass of each of the ions detected in mass spectrometry is converted into the molecular weight, or when the higher-level DB search portion 42, the lower-level DB search portion 45, the first search portion 46, and the second search portion 47 perform database search, molecular weights listed in each mass list (or partial mass list) in the database is converted into ion mass, and then the resultant mass list (or partial mass list) is compared with a test mass list (or test partial mass list).

REFERENCE SINGS LIST

1 . . . Mass Spectrometry Unit
11 . . . Ionizer
12 . . . TOF
2 . . . Cell Identification Unit
20 . . . Storage Section
21 . . . Higher-Level Database
22 . . . Lower-Level Database
22a, 22b, 22c . . . Sub-Database
23 . . . Database
24 . . . Variation Database
30 . . . Interface
40 . . . Computation Section
41 . . . Test mass List Creation Portion
42 . . . Higher-Level DB Search Portion
43 . . . Classification Group Determination Portion
44 . . . Test Partial Mass List Creation Portion
45 . . . Lower-Level DB Search Portion
46 . . . First Search Portion
47 . . . Second Search Portion
50 . . . Analysis Controller
61 . . . Display Section
62 . . . Operation Section

The invention claimed is:

1. An apparatus that identifies a type of a test cell based on a result obtained by performing mass spectrometry on the test cell, the apparatus comprising:
   a storage section that stores a database containing mass lists for a plurality of known cells, each of the mass lists listing ion mass values or molecular weights of constituent components of the known cell,
   a computation section that includes a processor configured to:
      a) search the database for a test mass list which is created based from a result of the mass spectrometry and which lists ion mass values or molecular weights of constituent components of the test cell,
      b) determine, based on a result of the search performed, a classification group to be searched in the following search operation,
      c) create a test partial mass list from the test mass list by deleting ion mass values or molecular weights common to the classification group determined, and
      d) search, among the mass lists contained in the database, mass lists for known cells which belong to the classification group determined for the test partial mass list, delete, from the mass lists to be searched, ion mass values or molecular weights common to the classification group determined, and search the mass lists having undergone the deletion operation for the test partial mass list; and
   an output device that outputs a result of searching the second database for the at least one partial mass list.

2. The cell identification apparatus according to claim 1, further comprising:
   a variation database containing information on variations that may occur in a base sequence or an amino acid sequence, and
   obtaining information on the variations from the variation database, changing, based on the information, the ion mass values or molecular weights contained in the mass lists having undergone the deletion operation to ion mass values or molecular weights after the variations occur, and searching the changed mass lists for the test partial mass lists.

3. A non-transitory computer readable medium recording a program that makes a computer function according to a method, comprising:
   searching the database for a test mass list which is created based from a result of a mass spectrometry and which lists ion mass values or molecular weights of constituent components of the test cell;

determining, based on a result of the search performed, a classification group to be searched in the following search operation;

creating a test partial mass list from the test mass list by deleting ion mass values or molecular weights common to the classification group determined;

searching, among the mass lists contained in the database, mass lists for known cells which belong to the classification group determined by the classification group determination means for the test partial mass list, deleting, from the mass lists to be searched, ion mass values or molecular weights common to the classification group determined, and searching the mass lists having undergone the deletion operation for the test partial mass list; and outputting a result of searching the second database for the at least one partial mass list.

* * * * *